(12) United States Patent
Chen et al.

(10) Patent No.: US 9,433,932 B2
(45) Date of Patent: Sep. 6, 2016

(54) HYDROGENATION CATALYST AND METHOD OF MANUFACTURING THE SAME

(71) Applicant: National Cheng Kung University, Tainan (TW)

(72) Inventors: Chuh-Yung Chen, Tainan (TW); Cheng-Chien Wang, Tainan (TW); Chi-Yuan Hung, Tainan (TW); Lin-Hsiang Huang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 14/517,350

(22) Filed: Oct. 17, 2014

(65) Prior Publication Data

US 2016/0059219 A1  Mar. 3, 2016

Related U.S. Application Data

(60) Provisional application No. 62/043,641, filed on Aug. 29, 2014.

(51) Int. Cl.

| | |
|---|---|
| *B01J 37/34* | (2006.01) |
| *B01J 23/00* | (2006.01) |
| *B01J 23/40* | (2006.01) |
| *B01J 23/42* | (2006.01) |
| *B01J 23/44* | (2006.01) |
| *B01J 23/89* | (2006.01) |
| *C07C 5/10* | (2006.01) |
| *C07C 67/303* | (2006.01) |

(52) U.S. Cl.
CPC .............. *B01J 23/892* (2013.01); *C07C 5/10* (2013.01); *C07C 67/303* (2013.01); *C07C 2101/14* (2013.01); *C07C 2101/16* (2013.01)

(58) Field of Classification Search
CPC ...... C01B 31/086; B01J 23/40; B01J 23/892
USPC ............ 502/5, 326, 337, 339; 977/773, 775
See application file for complete search history.

(56) References Cited

U.S. PATENT DOCUMENTS

| | | | | |
|---|---|---|---|---|
| 3,919,120 | A | * 11/1975 | Kato .................... | B01D 53/945 423/213.2 |
| 4,214,893 | A | * 7/1980 | Tsuganezawa ............ | B22F 9/24 148/105 |
| 5,362,465 | A | * 11/1994 | Iida ........................ | C01B 25/163 423/304 |
| 6,841,626 | B1 | 1/2005 | Wege et al. | |

(Continued)

FOREIGN PATENT DOCUMENTS

| | | |
|---|---|---|
| CN | 101815575 | 8/2010 |
| CN | 101289365 | 10/2011 |

*Primary Examiner* — Cam N. Nguyen
(74) *Attorney, Agent, or Firm* — Muncy, Geissler, Olds & Lowe, P.C.

(57) ABSTRACT

A hydrogenation catalyst is provided. The hydrogenation catalyst has a nanonickel carrier, and noble metal nanoparticles selected from Pd, Pt, Ru, Rh, or a mixture thereof, which are mounted onto the nanonickel carrier. Moreover, a method of manufacturing a hydrogenation catalyst is provided, and has steps of (1) preparing an aqueous solution containing nickel ions; (2) adding a first reducing agent in the aqueous solution containing nickel ions to form a reactant solution; (3) applying a magnetic field to the reactant solution for a first duration to obtain a nanonickel carrier; (4) preparing a noble metal solution; and (5) placing the nanonickel carrier in the noble metal solution for a second duration so that noble metal nanoparticles are mounted onto the nanonickel carrier.

21 Claims, 5 Drawing Sheets

(56) References Cited

U.S. PATENT DOCUMENTS

| | | | | |
|---|---|---|---|---|
| 7,375,053 B2 * | 5/2008 | Schmidt | ................ | C10G 47/12 |
| | | | | 502/313 |
| 7,569,513 B2 * | 8/2009 | Schmidt | ................ | C10G 47/12 |
| | | | | 502/259 |
| 7,648,938 B2 * | 1/2010 | Miyashita | ................ | B01J 23/42 |
| | | | | 502/180 |
| 7,819,939 B1 * | 10/2010 | Yang | ................ | B22F 9/24 |
| | | | | 423/138 |
| 8,785,065 B2 * | 7/2014 | Xu | ................ | B01J 35/0013 |
| | | | | 429/416 |
| 8,940,459 B2 * | 1/2015 | Nakanishi | ........... | H01M 4/8652 |
| | | | | 429/405 |
| 2009/0029190 A1 * | 1/2009 | Ohmori | ................ | G11B 5/667 |
| | | | | 428/831 |
| 2010/0196801 A1 * | 8/2010 | Nakanishi | ........... | H01M 4/8652 |
| | | | | 429/524 |
| 2011/0129743 A1 * | 6/2011 | Xu | ................ | B01J 23/892 |
| | | | | 429/416 |
| 2012/0164470 A1 * | 6/2012 | Leschkies | ............. | B82Y 40/00 |
| | | | | 428/607 |
| 2013/0035511 A1 | 2/2013 | Wolf et al. | | |
| 2013/0084385 A1 * | 4/2013 | Zhou | ................ | B22F 9/24 |
| | | | | 427/127 |
| 2013/0101920 A1 * | 4/2013 | Hiraiwa | ............. | H01M 4/8853 |
| | | | | 429/482 |

* cited by examiner

Fig. 5

HYDROGENATION CATALYST AND METHOD OF MANUFACTURING THE SAME

CROSS REFERENCE TO RELATED APPLICATIONS

This application claims priority benefit from U.S. Provisional Application No. 62/043,641, filed on Aug. 29, 2014, and the contents of which are incorporated herein by reference.

FIELD OF THE INVENTION

The present invention relates to a hydrogenation catalyst and a method of manufacturing the hydrogen catalyst, and more particularly to a hydrogenation catalyst with magnetism and a method of manufacturing the same.

BACKGROUND OF THE INVENTION

In general, metal catalysts are frequently used in the hydrogenation system of aromatic compounds. Compared with other catalytic reactions using non-metallic catalysts, metal catalysts are not only clean but also have a low impact on the economy and the environment. In addition, noble metals such as palladium, ruthenium, rhodium, and platinum have been demonstrated to have high catalytic activities in a hydrogen atmosphere.

For example, Bayer Corporation published in the United States Patent Publication No. 2005 6,841,626B1 that a noble metal, such as platinum (Pt) and palladium (Pd), is used as a catalyst, $SiO_2$ and $Al_2O_3$ as a catalyst carrier, and cyclohexane as a solvent to carry out the hydrogenation reaction of polystyrene. The hydrogenation reaction of polystyrene catalyzed by $Pt/SiO_2$ catalyst at a pressure of 875 bar, and a temperature of 150° C. can obtain a hydrogenation rate of 98.4%. While the hydrogenation reaction of polystyrene catalyzed by $Pd/Al_2O_3$, a hydrogenation rate approaches 100% under a pressure of 100 bar at a temperature of 200° C.

In addition, Bayer Corporation mentioned in China Patent No. 101,815,575 issued in 2010 that the catalyst used in the gas phase reaction can catalyze the hydrogenation of nitrobenzene to become aniline. The method includes steps of mixing 106.4 mg palladium chloride ($PdCl_2$), 6 ml hydrochloric acid (HCl), and 294 ml distilled water to obtain 300 ml palladium chloride acid ($H_2PdCl_4$). In step (a), the mixed solution of 15 ml $H_2PdCl_4$ and 31.5 ml water and 3.5 ml methanol was added 33.25 mg polyvinylpyrrolidone (PVP-40), refluxed at 80° C. for 3 hours. Next, in step (b), 0.6 ml tetraethoxysilane (TEOS) was mixed with 7 ml ethanol. Subsequently, the mixed solution in step (a) was stirred violently, and a mixture of ethanol-ammonia ($NH_3$) was added therein, then the mixture of ethanol-TEOS was quickly added therein, too. After stirring overnight at room temperature, the precipitation was washed with ethanol, and Pd—$SiO_2$ nanoparticles were obtained by centrifugation. In step (c), 0.43 g alcohol-polyethylene glycol ether (such as Marlipal) was dissolved in water to prepare an aqueous solution of Marlipal. Next, the Pd—$SiO_2$ nanoparticles obtained in step (b) were dispersed in 40 g ethanol and heated to 30° C. Subsequently, the aqueous solution of Marlipal was added to 30° C. Pd—$SiO_2$ solution, 0.45 ml zirconium n-butoxide was added therein and stirred for 4 hours. The liquid phase with dispersion was replaced by water. Then, the solids were obtained by calcining at 900° C. The Pd—$SiO_2$—$ZrO_2$ particles obtained in step (c) were stirred in 50 ml solution containing 1 mole sodium hydroxide (NaOH) for 3 hours, then centrifuged and washed with a solution containing 1 mole NaOH. Finally, Pd—$ZrO_2$ was obtained after drying at room temperature.

Furthermore, Zhu et al. taught in Chinese Patent No. CN101289365 published in 2011 that 0.12 g nitrate tetraammine platinum ($Pt(NH_3)_4(NO_3)_2$) and 7.4 g hexahydrate cobalt nitrate ($Co(NO_3)_2 \cdot 6H_2O$) were dissolved in 200 ml deionized water, and 3.5 g of the $SiO_2$ carrier was added. After stirring for 2 hours, the mixture is dried in a water bath at 95° C., and then calcined at 550° C. to obtain a catalyst. The catalyst was placed in a reactor having a mixed atmosphere of hydrogen and nitrogen with a flow rate at 10 ml/min and 40 ml/min, and the benzene was fed with a flow rate at 0.5 ml/hrs. The conversion of benzene was 63% when the reaction temperature was 84° C.

However, the noble metals of the abovementioned hydrogenation catalysts are mounted onto aluminum oxide ($Al_2O_3$) or silica ($SiO_2$), and the catalysts need to be separated from the required product by filtration after the reaction. It is difficult to recover the catalyst when the particles are too small to filter. Furthermore, since platinum is a very rare and expensive metal catalyst for general chemical reactions, the recovery of noble metal catalysts and recovery efficiency are important for reducing process costs to enhance efficiency and save resources.

It is therefore necessary to provide a hydrogenation catalyst and a method of manufacturing the hydrogenation catalyst capable of being recovered easily, in order to solve the problems existing in the conventional technology as described above.

SUMMARY OF THE INVENTION

A primary object of the present invention is to provide a hydrogenation catalyst including nickel nanowires which has a high specific surface area. In addition, noble metal nanoparticles are introduced to improve the catalytic performance of the hydrogenation catalyst. When using a hydrogenation catalyst with magnetism in petrochemicals, polymers, or special high-value chemicals production, the hydrogenation catalyst can be recovered easily by its magnetism to solve the problem of traditional nanocatalysts, which are difficult to reuse, and greatly reduces material costs.

The secondary object of the present invention is to provide a method of manufacturing a hydrogenation catalyst. First, by referring to a chemical reduction reaction, the nanocrystalline nickel is self-assembled to form one-dimensional nanowires in a simple magnetic field accompanying with electroless plating to produce a magnetic carrier. Subsequently, noble metal nanoparticles grow on nickel by additional reducing agents or different an oxidization/reduction potential between two metals themselves without additional reducing agents. The method of manufacturing the hydrogenation catalyst is simple, and does not require complex pretreatment, and therefore production costs can be reduced.

To achieve the above objects, the present invention provides a hydrogenation catalyst, comprising a nanonickel carrier; and noble metal nanoparticles selected from palladium, platinum, ruthenium, rhodium, or a mixture thereof, wherein the noble metal nanoparticles are mounted onto the nanonickel carrier.

In one embodiment of the present invention, the nanonickel carrier is constituted by one-dimensional nickel nanowires.

In one embodiment of the present invention, a specific surface area of the nanonickel carrier is greater than or equal to 0.2 m²/g.

In one embodiment of the present invention, a weight percentage of the noble metal nanoparticles in the hydrogenation catalyst is 2.5-7%.

In one embodiment of the present invention, an atomic percentage of the noble metal nanoparticles in the hydrogenation catalyst is 1.5-2.5%.

In one embodiment of the present invention, a specific surface area of the hydrogenation catalyst is greater than or equal to 3.0 m²/g.

Furthermore, the present invention provides a method of manufacturing a hydrogenation catalyst, comprising the steps of: (1) preparing an aqueous solution containing nickel ions; (2) adding a first reducing agent in the aqueous solution containing nickel ions to form a reactant solution; (3) applying a magnetic field to the reactant solution for a first duration to obtain a nanonickel carrier; (4) preparing a noble metal solution containing noble metal ions selected from palladium ions, platinum ions, ruthenium ions, rhodium ions, or a mixture thereof; and (5) placing the nanonickel carrier in the noble metal solution for a second duration so that noble metal nanoparticles are mounted onto the nanonickel carrier.

In one embodiment of the present invention, the aqueous solution containing nickel ions in the step (1) is prepared from nickel chloride and deionized water.

In one embodiment of the present invention, the aqueous solution containing nickel ions further comprises an assistant agent selected from carboxymethyl cellulose (CMC), sodium citrate, sodium hydroxide, or a mixture thereof.

In one embodiment of the present invention, carboxymethyl cellulose is 4-6% by weight in the aqueous solution containing nickel ions.

In one embodiment of the present invention, the step (1) further comprises a step (1a) of: heating and stirring until the assistant agent is totally dissolved in the aqueous solution containing nickel ions.

In one embodiment of the present invention, the first reducing agent is hydrazine.

In one embodiment of the present invention, the magnetic field is 500-5000 G (Gauss).

In one embodiment of the present invention, the first duration is 1-3 hours.

In one embodiment of the present invention, the noble metal solution containing noble metal ions in the step (4) is prepared from a noble metal salt and hydrochloric acid.

In one embodiment of the present invention, the concentration of the hydrochloric acid is 10 N (mole/Kg).

In one embodiment of the present invention, the noble metal solution containing noble metal ions further comprises an additive selected from sodium citrate, sodium hydroxide, or a mixture thereof.

In one embodiment of the present invention, the step (4) further comprises a step (4a) of: heating and stirring until the additive is totally dissolved in the aqueous solution containing noble metal ions.

In one embodiment of the present invention, the step (5) further comprises a step of adding a second reducing agent to facilitate the formation of the noble metal nanoparticles.

In one embodiment of the present invention, the second reducing agent is hydrazine.

In one embodiment of the present invention, the second duration is 1-3 hours.

DESCRIPTION OF THE DRAWINGS

FIGS. 2a-2b are views of the SEM observation of the hydrogenation catalyst according to one embodiment of the present invention (10 kV, 1,000 X-100,000 X), where FIG. 2a shows platinum on nickel nanowires (respectively by 1 k, 30 k, 50 k, 100 kX from right to left, and from bottom to top), FIG. 2b shows palladium on nickel nanowires (respectively by 1 k, 30 k, 50 k, 100 kX from right to left, and from bottom to top).

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, if there is no specific description in the invention, singular terms such as "a", "one", and "the" include the plural number. For example, "a compound" or "at least one compound" may include a plurality of compounds, and the mixtures thereof. If there is no specific description in the invention, the "%" means "weight percent (wt %)", and the numerical range (e.g. 10%-11% of A) contains the upper and lower limit (i.e. 10%≤A≤11%). If the lower limit is not defined in the range (e.g. less than, or below 0.2% of B), it means that the lower limit is 0 (i.e. 0%≤B≤0.2%). The proportion of "weight percent" of each component can be replaced by the proportion of "weight portion" thereof. The abovementioned terms are used to describe and understand the present invention, but the present invention is not limited thereto.

A hydrogenation catalyst is provided according to one embodiment of the present invention, which comprises a carrier made of nano nickel, and noble metal nanoparticles selected from palladium (Pd), platinum (Pt), ruthenium (Ru), Rhodium (Rh), or a mixture thereof. The noble metal nanoparticles connect to at least a portion of the surface of the nanonickel carrier. The noble metal nanoparticles are capable of catalyzing hydrogenation reactions, and therefore unsaturated bonds in carbon chains (mainly double bonds between two carbon atoms) are converted to saturated carbon-to-carbon bonds. The nanonickel carrier may be, for example, constituted by one-dimensional nickel nanowires. When the nanonickel carrier is constituted by one-dimensional nickel nanowires, it has a specific surface area greater than or equal to 0.29 m²/g, for example 0.30 m²/g, 0.32 m²/g, or 0.35 m²/g, but it is not limited thereto. Preferably, a weight percentage of the noble metal nanoparticles in the hydrogenation catalyst is 2.5-7%, for example 2.9%, 3.5%, or 6.4%, but it is not limited thereto. Preferably, an atomic percentage of the noble metal nanoparticles in the hydrogenation catalyst is 1.5-2.5%, for example 1.6%, 2.1%, or 2.3%, but it is not limited thereto. In addition, a specific surface area of the hydrogenation catalyst is greater than or equal to 3.0 $m^2/g$. Preferably, the hydrogenation catalyst has a high specific surface area in a range of 3.5-4.5 $m^2/g$, for example, 3.7 $m^2/g$ or 4.3 $m^2/g$, but it is not limited thereto.

Furthermore, a method of manufacturing a hydrogenation catalyst according to one embodiment of the present invention is provided, and mainly comprises the steps of (S1) preparing an aqueous solution containing nickel ions; (S2) adding a first reducing agent in the aqueous solution containing nickel ions to form a reactant solution; (S3) applying a magnetic field to the reactant solution for a first duration to obtain a nanonickel carrier; (S4) preparing a noble metal solution containing noble metal ions selected from palladium ions, platinum ions, ruthenium ions, rhodium ions, or a mixture thereof; and (S5) placing the nanonickel carrier in the noble metal solution for a second duration so that noble metal nanoparticles are mounted onto the nanonickel carrier. The principle and the implementation details of each step in this embodiment of the present invention will be described in detail hereinafter.

First, the method of manufacturing a hydrogenation catalyst according to a preferred embodiment of the present invention is the step (S1): preparing an aqueous solution containing nickel ions. In this step, the aqueous solution containing nickel ions can be prepared from nickel salts and deionized water. The nickel salts may be, for example, nickel chloride, nickel nitrate, or nickel hydroxide. The aqueous solution containing nickel ions further comprises an assistant agent selected from carboxymethyl cellulose (CMC), sodium citrate, sodium hydroxide, or a mixture thereof. The amount of the added CMC in the aqueous solution containing nickel ions is 4 to 6% by weight, for example 4.5%, 5%, or 6%, but it is not limited thereto. The amount of the added sodium citrate in the aqueous solution containing nickel ions is 5-9%. The amount of the added sodium hydroxide in the aqueous solution containing nickel ions is 0.5-2% by weight. If the assistant agent is a solid, a further step of (S1a): heating and stirring until the assistant agent is totally dissolved in the aqueous solution containing nickel ions, is preferably adopted.

Next, the method of manufacturing a hydrogenation catalyst according to one embodiment of the present invention is the step (S2): adding a first reducing agent in the aqueous solution containing nickel ions to form a reactant solution. In this step, the first reducing agent is hydrazine or hydrogen peroxide, for example. In addition, the weight percentage of the added first reducing agent in the aqueous solution containing nickel ions is 3-9%, for example 3%, 6% or 9%, but it is not limited thereto.

Next, the method of manufacturing a hydrogenation catalyst according to one embodiment of the present invention is the step (S3): applying a magnetic field to the reactant solution for a first duration to obtain a nanonickel carrier. In this step, the magnetic field is 500-5000 G. The first duration is 1-3 hours, for example 1, 1.5, or 2.5 hours, but it is not limited thereto.

Next, the method of manufacturing a hydrogenation catalyst according to one embodiment of the present invention is the step (S4): preparing a noble metal solution containing noble metal ions selected from palladium ions, platinum ions, ruthenium ions, rhodium ions, or a mixture thereof. In this step, the noble metal solution containing noble metal ions can be prepared by noble metal salts and hydrochloric acid (HCl). The noble metal salts may be, for example, palladium chloride, palladium bromide, palladium nitrate, or dihydrogen hexachloroplatinate (IV) hexahydrate. The concentration of the hydrochloric acid may be, for example, 10N (Molality, mole/Kg), but it is not limited thereto. The noble metal solution containing noble metal ions may further contain an additive selected from sodium citrate, sodium hydroxide, or a mixture thereof. The amount of the added sodium citrate in the noble metal solution containing noble metal ions is 5-9%. The amount of the added sodium hydroxide in the noble metal solution containing noble metal ions is 0.5-2% by weight. If the additive is a solid, a further step of (S4a): heating and stirring until the additive is totally dissolved in the noble metal solution containing noble metal ions, is preferably adopted.

Lastly, the method of manufacturing a hydrogenation catalyst according to one embodiment of the present invention is the step (S5): placing the nanonickel carrier in the noble metal solution for a second duration so that noble metal nanoparticles are mounted onto the nanonickel carrier. In this step, the noble metal nanoparticles are formed by reducing the noble metal ions through the nanonickel carrier (i.e., the different oxidization/reduction potential between two metals themselves can be used without additional reducing agents to achieve the reduction of the noble metal ions, but the reaction is slower), or by adding a second reducing agent in the noble metal solution containing noble metal ions to accelerate the formation of the noble metal nanoparticles. The second reducing agent is hydrazine or hydrogen peroxide, for example. In addition, the weight percentage of the added second reducing agent in the noble metal solution containing noble metal ions is 3-9%, for example 3%, 6%, or 9%, but it is not limited thereto. The second duration is 1-3 hours, for example 1, 1.5 or 2.5 hours, but it is not limited thereto.

To make the hydrogenation catalyst and the method for manufacturing the hydrogenation catalyst of the present invention more definite, please refer to the actual manufacturing process described in the following. The exemplified preparation of the catalyst is not used to restrict to the composition and the manufacturing method thereof.

Figure 1A:
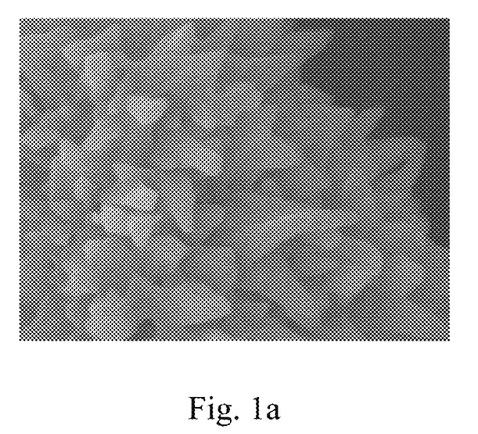
FIGS. 1a-1c are views of the scanning electron microscope (SEM) observation of the nanowires prepared according to one embodiment of the present invention (10 kV, by 10 kX, 50 kX, 100 kX).
Figure 1B:
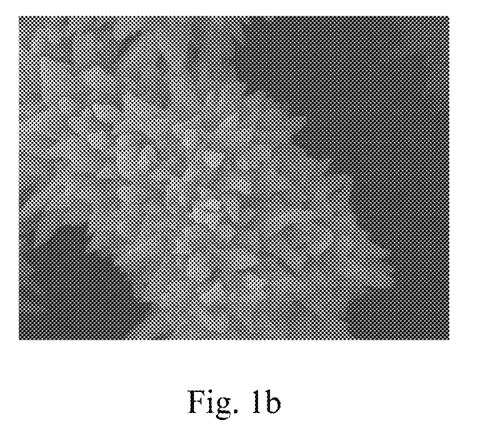
Figure 1C:
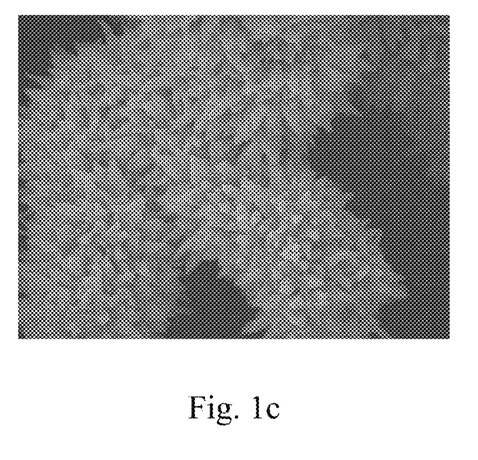

In a preferred embodiment of the invention, first, preparing the nanonickel carrier by the following steps:

Using 1.2 g of nickel chloride and 50 ml of deionized water to form an aqueous solution, and then 2.5 g of carboxymethyl cellulose (CMC) is added therein. The amount of the added CMC in the total weight is about 5%. Next, 3.5 g of sodium citrate and 0.4 g of sodium hydroxide are sequentially added in the aqueous solution, and the aqueous solution is stirred at 80° C. to completely dissolve the solids therein. Next, 2 ml of hydrazine is added to form a mixture (a). A fixed magnetic field is applied to the mixture (a), and a reduction reaction is performed for 2 hours. After the reaction is finished, the product is washed by 70° C. deionized water for removing CMC, and the nickel nanowires are obtained. The nickel nanowires are stored in ethanol before use. FIGS. 1a-1c show the nickel nanowires observed by SEM. A specific surface area calculated by BET method of the nickel nanowires is around 0.298 $m^2/g$ (i.e., Adsorption theory proposed by Stephen Brunauer, Paul Hugh Emmett, and Edward Teller, referred hereafter as BET).

Next, platinum nanoparticles are grown on the nickel nanowires to form a Pt/Ni hydrogenation catalyst, and the steps thereof are as below.

Preparing an aqueous solution of dihydrogen hexachloroplatinate (IV) hexahydrate ($H_2PtCl_6 \cdot (H_2O)_6$) containing

Figure 2A:
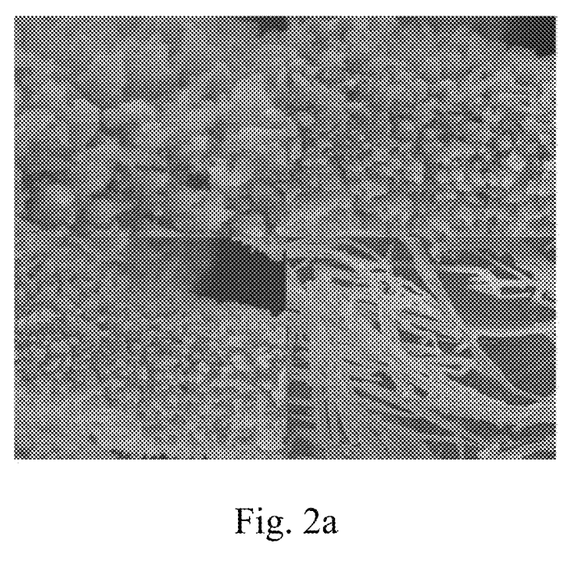

0.4 g platinum ions per 100 ml, for example, 0.03 g dihydrogen hexachloroplatinate (IV) hexahydrate is dissolved in 7.5 ml of deionized water at 70° C. Then, 0.5 g Na$_3$C$_6$H$_5$O$_7$ (sodium citrate), 0.4 g NaOH (sodium hydroxide), and 20 ml deionized water are added in 7.5 ml of the aqueous solution of dihydrogen hexachloroplatinate (IV) hexahydrate, and stirred at 60° C. until the added solids are dissolved to obtain a mixture (b). 1 g nickel nanowires are placed into the mixture (b), and 12 ml of N$_2$H$_4$ (Hydrazine) is added therein as a reducing agent. After 2 hours, the precipitation is washed by 70° C. deionized water several times to purify the Pt/Ni hydrogenation catalyst. The Pt/Ni hydrogenation catalyst is stored in acetone solvent before use. FIG. 2a shows the Pt/Ni hydrogenation catalyst observed by SEM. In addition, a specific surface area calculated by BET method of the Pt/Ni hydrogenation catalyst is around 4.36 m$^2$/g. The weight percentage of the platinum nanoparticles in the Pt/Ni hydrogenation catalyst is 6.4%, the atomic percentage of the platinum nanoparticles in the Pt/Ni hydrogenation catalyst is 2.02%.

Alternatively, the platinum nanoparticles could be replaced by palladium (Pd) nanoparticles on the nickel nanowires to produce a Pd/Ni hydrogenation catalyst, and the steps thereof are as below.

Figure 2B:
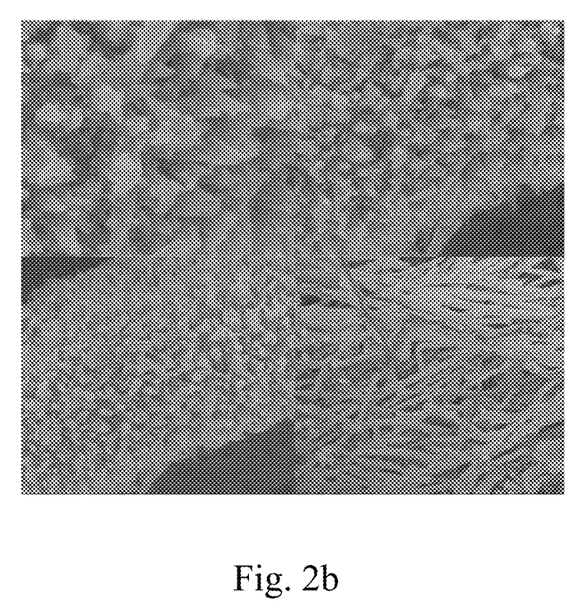

Preparing 100 ml of 10 N HCl, and adding 1.77 g of palladium chloride in the hydrochloric acid solution, then stirring at 70° C. until the added solids are dissolved to form an aqueous solution of palladium chloride. Next, 3 g of sodium citrate and 2.4 g of sodium hydroxide are added in 180 ml of the aqueous solution of palladium chloride, and stirred at 60° C. until they are dissolved to form a mixture (c). 1 g nickel nanowires are placed into the mixture (c), and 12 ml of N$_2$H$_4$ (Hydrazine) is added therein as a reducing agent. After 2 hours, the precipitation is washed by 70° C. deionized water several times to purify the Pd/Ni hydrogenation catalyst. The Pd/Ni hydrogenation catalyst is stored in an acetone solvent before use. FIG. 2b shows the Pt/Ni hydrogenation catalyst observed by SEM. In addition, a specific surface area calculated by BET method of the Pd/Ni hydrogenation catalyst is 3.77 m$^2$/g. The weight percentage of the palladium nanoparticles in the Pd/Ni hydrogenation catalyst is 2.93%, the atomic percentage of the palladium nanoparticles in the Pd/Ni hydrogenation catalyst is 1.64%.

In order to verify the hydrogenation efficiency of the hydrogenation catalyst according to the present invention, the following experiments and analysis of the hydrogenated products are carried out.

Figure 3:
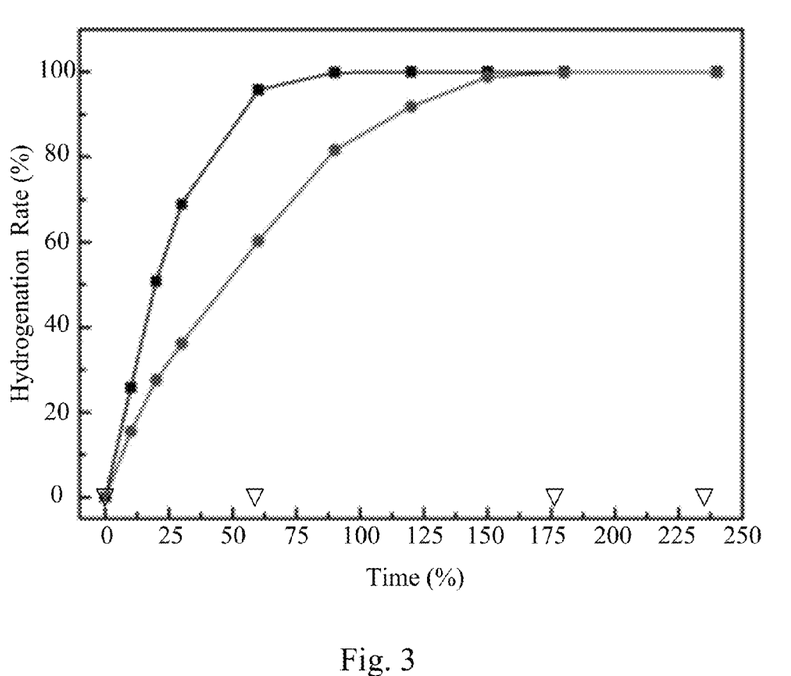
FIG. 3 shows the catalytic efficiency of Pd/Ni in the hydrogenation of toluene under different pressures of a hydrogen atmosphere. (■: 70 Kg; ●: 50 Kg; ▽: 70 Kg with pure Ni nanowire as a control group)

Please refer to FIG. 3, which shows the catalytic efficiency of Pd/Ni in the hydrogenation of toluene under different pressure of hydrogen atmosphere. The hydrogenation reaction of toluene is as shown below:

First, 50 g toluene was placed into a reaction vessel, and then Pd/Ni hydrogenation catalyst or pure nickel wire (control group) with an amount by 5 wt % of toluene was added. The foregoing mixture were stirred at 1000 rpm, and purged with nitrogen (at a pressure ranged from 30 to 40 psi) for 10-15 minutes to remove oxygen in the reaction vessel. After purged with nitrogen, the reaction vessel was purged with hydrogen (at a pressure ranged from 30 to 40 psi) for 10-15 minutes to remove nitrogen in the reaction vessel. Subsequently, the hydrogen pressure was set to 70, or 50 Kg/cm$^2$; the reaction temperature was at 180° C. The hydrogenated product was sampled at different times during the reaction, and analyzed by gas chromatography (GC) to obtain a real time conversion. After the reaction has been completed, the reaction vessel was purged with nitrogen (at a pressure ranged from 30 to 40) for 10-15 minutes to remove remaining hydrogen in the reaction vessel. Subsequently, the catalyst was separated from the product by a powerful magnet, and the recovery of the catalyst was over 96%.

From FIG. 3, toluene is catalyzed by the Pd/Ni hydrogenation catalyst to form methyl cyclohexane. When the reaction was carried out at 180° C. under 70 Kg/cm$^2$ of hydrogen pressure, toluene was completely converted into methyl cyclohexane during reacting for 100 minutes. When the reaction was carried out at 180° C. under 50 Kg/cm$^2$ of hydrogen pressure, toluene was also completely hydrogenated during reacting for 150 minutes. In contrast, when using pure nickel nanowires as a hydrogenation catalyst, the hydrogenation reaction has almost no progress.

Figure 4:
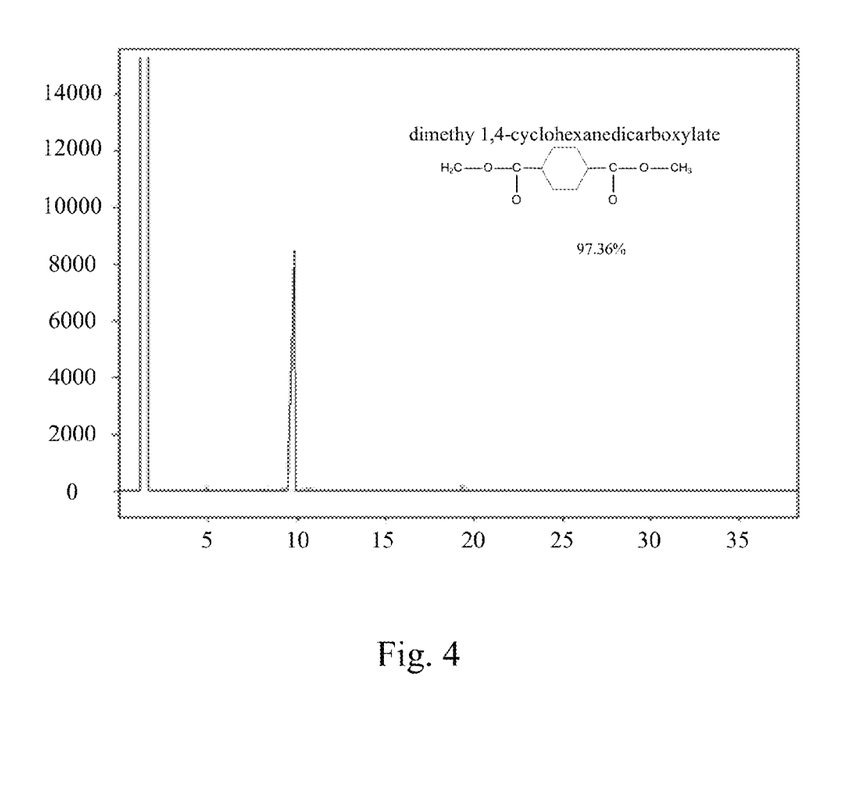
FIG. 4 is a gas chromatography (GC) spectrum of the product obtained from hydrogenation of dimethyl terephthalate (DMT) with the hydrogenation catalyst according to one embodiment of the present invention.

Please refer to FIG. 4, which shows a gas chromatography (GC) spectrum of the product obtained from hydrogenation of dimethyl terephthalate (DMT) with the Pd/Ni hydrogenation catalyst according to one embodiment of the present invention. The hydrogenation reaction of DMT is as below.

The remaining steps and reaction conditions were the same as the abovementioned hydrogenation reaction of toluene except that the reactants were 7.5 g DMT and 42.5 g ethyl acetate, the hydrogen pressure was 60 Kg/cm$^2$, and the reaction temperature was 200° C. After the reaction was carried out for 180 minutes, the hydrogenation rate was 90%, the purity was 97.36%, and the recovery of the catalyst was over 96%.

Figure 5:
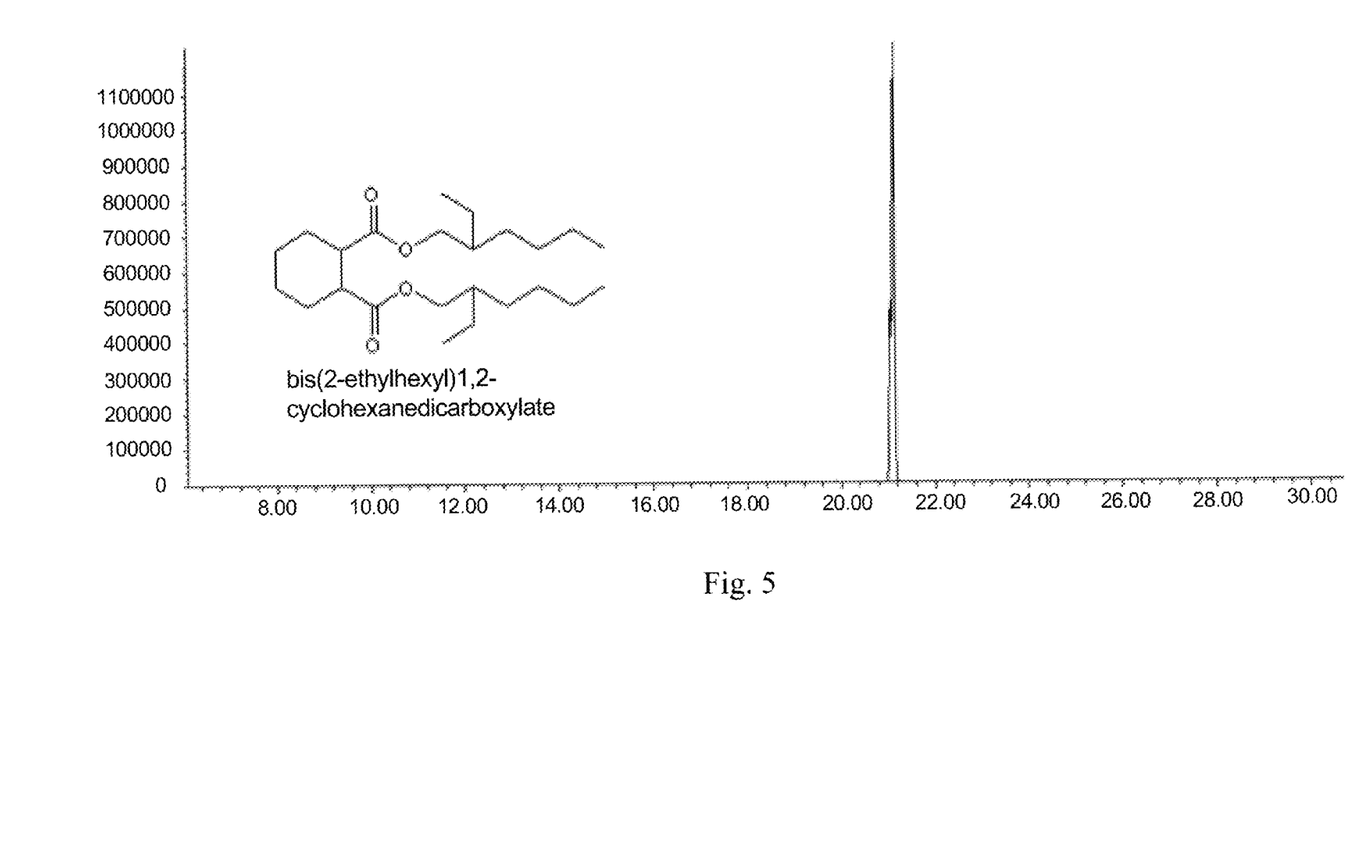
FIG. 5 is a GC spectrum of the product obtained from hydrogenation of dioctyl phthalate (DOP) with the hydrogenation catalyst according to one embodiment of the present invention.

Please continue referring to FIG. 5, which shows a gas chromatography (GC) spectrum of the product obtained from hydrogenation of dioctyl phthalate (DOP) with the Pd/Ni hydrogenation catalyst according to one embodiment of the present invention. The hydrogenation reaction of DOP is as below.

-continued

The remaining steps and reaction conditions were the same as the abovementioned hydrogenation reaction of toluene except that the reactants was 50 g DOP, the hydrogen pressure was 60 Kg/cm$^2$, and the reaction temperature was 200° C. After completing the reaction, the hydrogenation rate was 90%, and the recovery of the catalyst was over 96%.

Furthermore, in the hydrogenation reaction of polystyrene (PS) with Pd/Ni hydrogenation catalyst, the remaining steps and reaction conditions were the same as the abovementioned hydrogenation reaction of toluene except that the reactants were 5 g PS and 45 g cyclohexane, the hydrogen pressure was 200 psi, and the reaction temperature was 80° C. After the reaction was carried out for 30 minutes, the hydrogenation rate was confirmed as more than 80%.

Compared with conventional techniques, the hydrogenation catalyst and the method of manufacturing a hydrogenation catalyst in accordance with the present invention introduce the noble metal nanoparticles to improve the catalytic performance of the hydrogenation catalyst. In addition, the hydrogenation catalyst can be easily recovered by magnetism to solve the problem of a nanocatalyst which is difficult to reuse, and greatly reduces material costs. Moreover, the process of manufacturing the hydrogenation catalyst is simple, and does not require complex pretreatment, and therefore the production cost can be reduced.

The present invention has been described with preferred embodiments thereof and it is understood that many changes and modifications to the described embodiments can be carried out without departing from the scope and the spirit of the invention that is intended to be limited only by the appended claims.

What is claimed is:
1. A hydrogenation catalyst, comprising:
   a nanonickel carrier; and
   noble metal nanoparticles selected from palladium, platinum, ruthenium, rhodium, or a mixture thereof,
   wherein the noble metal nanoparticles are mounted onto the nanonickel carrier.
2. The hydrogenation catalyst according to claim 1, wherein the nanonickel carrier is constituted by one-dimensional nickel nanowires.
3. The hydrogenation catalyst according to claim 1, wherein a specific surface area of the nanonickel carrier is greater than or equal to 0.2 m$^2$/g.
4. The hydrogenation catalyst according to claim 1, wherein a weight percentage of the noble metal nanoparticles in the hydrogenation catalyst is 2.5-7%.
5. The hydrogenation catalyst according to claim 1, wherein an atomic percentage of the noble metal nanoparticles in regard to the hydrogenation catalyst is 1.5-2.5%.
6. The hydrogenation catalyst according to claim 1, wherein a specific surface area of the hydrogenation catalyst is greater than or equal to 3.0 m$^2$/g.
7. A method of manufacturing a hydrogenation catalyst, comprising steps of:
   (1) preparing an aqueous solution containing nickel ions;
   (2) adding a first reducing agent in the aqueous solution containing nickel ions to form a reactant solution;
   (3) applying a magnetic field to the reactant solution for a first duration to obtain a nanonickel carrier;
   (4) preparing a noble metal solution containing noble metal ions selected from palladium ions, platinum ions, ruthenium ions, rhodium ions, or a mixture thereof; and
   (5) placing the nanonickel carrier in the noble metal solution for a second duration so that noble metal nanoparticles are mounted onto the nanonickel carrier.
8. The method according to claim 7, wherein the aqueous solution containing nickel ions in the step (1) is prepared from nickel chloride and deionized water.
9. The method according to claim 7, wherein the aqueous solution containing nickel ions further comprises an assistant agent selected from carboxymethyl cellulose, sodium citrate, sodium hydroxide, or a mixture thereof.
10. The method according to claim 9, wherein carboxymethyl cellulose is 4-6% by weight in the aqueous solution containing nickel ions.
11. The method according to claim 9, wherein the step (1) further comprises a step (1a) of: heating and stirring until the assistant agent is totally dissolved in the aqueous solution containing nickel ions.
12. The method according to claim 7, wherein the first reducing agent is hydrazine.
13. The method according to claim 7, wherein the magnetic field is 500-5000 G.
14. The method according to claim 7, wherein the first duration is 1-3 hours.
15. The method according to claim 7, wherein the noble metal solution containing noble metal ions in the step (4) is prepared from a noble metal salt and hydrochloric acid.
16. The method according to claim 15, wherein the concentration of the hydrochloric acid is 10 N.
17. The method according to claim 7, wherein the noble metal solution containing noble metal ions further comprises an additive selected from sodium citrate, sodium hydroxide, or a mixture thereof.
18. The method according to claim 17, wherein the step (4) further comprises a step (4a) of: heating and stirring until the additive is totally dissolved in the aqueous solution containing noble metal ions.
19. The method according to claim 7, wherein the step (5) further comprises a step of adding a second reducing agent to facilitate the formation of the noble metal nanoparticles.
20. The method according to claim 19, wherein the second reducing agent is hydrazine.
21. The method according to claim 7, wherein the second duration is 1-3 hours.

* * * * *